(12) United States Patent
Ward (10) Patent No.: US 8,127,627 B2
(45) Date of Patent: Mar. 6, 2012

(54) DEVICE FOR COLLECTING SAMPLES AND METHOD OF USE

(75) Inventor: N. Robert Ward, Bothell, WA (US)

(73) Assignee: World Bioproducts, LLC, Bothell, WA (US)

( * ) Notice: Subject to any disclaimer, the term of this patent is extended or adjusted under 35 U.S.C. 154(b) by 455 days.

(21) Appl. No.: 12/478,296

(22) Filed: Jun. 4, 2009

(65) Prior Publication Data

US 2010/0307266 A1  Dec. 9, 2010

(51) Int. Cl.
*G01N 1/04* (2006.01)
(52) U.S. Cl. .................................................. 73/864.71
(58) Field of Classification Search ............... 73/864.71
See application file for complete search history.

(56) References Cited

U.S. PATENT DOCUMENTS

| | | | |
|---|---|---|---|
| 3,508,547 A | 4/1970 | Deuschle | |
| 3,815,580 A | 6/1974 | Oster | |
| 4,027,658 A | 6/1977 | Marshall | |
| 4,136,680 A * | 1/1979 | Southworth | 600/572 |
| 4,175,439 A | 11/1979 | Laker | |
| 4,803,998 A * | 2/1989 | Kezes et al. | 600/572 |
| 4,856,136 A | 8/1989 | Janssen | |
| 4,934,011 A | 6/1990 | Haug | |
| 5,341,538 A | 8/1994 | Banome | |
| 5,370,128 A | 12/1994 | Wainwright | |
| 5,477,863 A | 12/1995 | Grant | |
| 5,991,960 A | 11/1999 | Johnson | |
| 6,021,681 A | 2/2000 | Jezek | |
| 6,383,804 B1 | 5/2002 | Ward, Jr. et al. | |
| 7,270,959 B2 * | 9/2007 | Hudak | 435/7.1 |
| 7,300,633 B2 * | 11/2007 | Hudak et al. | 422/537 |

* cited by examiner

*Primary Examiner* — Hezron E Williams
*Assistant Examiner* — Rodney T Frank
(74) *Attorney, Agent, or Firm* — Christensen O'Connor Johnson Kindness PLLC (57) ABSTRACT

The present invention comprises a sampling device for collecting samples having a detachable handle with a threaded portion. The device for collecting samples is further provided having a connecting head with a receiving member whereby the receiving member detachably engages the threaded portion of the handle. An absorbent material is placed about the connecting head wherein the absorbent material is a single piece of generally rectangular material folded at a distal edge of the connecting head and adhered through at least one aperture of the connecting head. The detachable handle with the threaded portion is releasably attached to a connecting head with an absorbent material by rotating the detachable handle into the connecting head in a clockwise direction. The user can rotate the handle in a counter-clockwise direction and easily release the handle from the connecting head with the absorbent material into the collection bag.

24 Claims, 6 Drawing Sheets

DEVICE FOR COLLECTING SAMPLES AND METHOD OF USE

FIELD OF THE INVENTION

The present invention relates to sampling devices, and more particularly to a device for collecting samples that is ideally suited for use in sterile collection in preventing and monitoring contamination of certain areas.

BACKGROUND OF INVENTION

For sterile collection, it is necessary to collect samples for testing and monitor for any microbial contamination. Microorganisms, such as *Listeria monocytogenes*, can reside in biofilms, or have strong attachments to industrial surfaces that afford protection to these types of pathogenic or disease-causing microorganisms from sanitizing agents, competition from other microorganisms, mechanical removal, and environmental stressors, such as drying or UV exposure.

Food manufacturers have a need to continuously monitor and collect samples, particularly in production areas, in order to avoid outbreaks or to produce food products with little to no microbial contamination. It is commonly known that pathogenic microorganisms in the production environment may contribute to contamination of the food products being produced. Consequently, surfaces in the production areas where samples are routinely collected include ceilings, floors, walls, drains, and equipment. Improper or incomplete sampling of a surface may lead to inaccurate and false results for microbial safety in the production environment and potentially result in contamination of the food products during production.

It is crucial that the device for collecting samples be robust and durable to avoid any mishap that could stop or delay production. A mishap can easily occur if the device for collecting samples, or a portion of the collection device, breaks in hard-to-reach areas or is inadvertently dropped into a cooking vessel or a storage tank. Similarly, if the collection device breaks or fragments during sample collection, pieces of the collection device can easily enter the food during production. Furthermore, an improperly designed collection device could become wedged or caught in hard-to-reach areas of production equipment, and removal could require disassembling the production equipment.

Typically, the device for collecting samples has a swab of absorbent material attached on the distal portion of the device that is rubbed onto or scrubbed against a sampling surface for collecting the sample. Such swabs of cotton, dacron, alginate, or foam on a swab stick handle made of wood or plastic are commonly used to collect the sample. After collecting the sample, the swab is placed into a sterile test tube or a collection bag for later testing and processing. The swabs are normally suited for small clinical sampling surface areas such as the throat, while industrial sampling surfaces require stronger and bigger collection devices. The swab may be effective in accessing hard-to-reach areas because of its thin profile, however, it is inefficient when sampling a larger industrial area such as a conveyor belt or floor. Further, the user collecting the sample is required to press down firmly and to scrub the surfaces of a food production area to disrupt biofilms that are formed by microorganisms. A failure to disrupt and collect a biofilm during sampling can result in a false negative determination. The swabs may easily break when rubbing and lifting the biofilm to obtain a good sample from an industrial surface.

Sometimes a sponge is held directly by the user in collecting a sample. Direct handling of pre-moistened sponges is described in the U.S. Department of Agriculture (USDA) methods for sampling and testing cattle carcasses for *Salmonella* and *Escherichia coli*. However, these sponges are susceptible to mishandling by the user, resulting in contamination of the sample and inaccurate results. The user may easily contaminate the sample by touching the sponge.

Alternative swab devices have been developed for collection of samples, such as the device described in U.S. Pat. No. 6,383,804, wherein a sampling device with a snap-off head includes an elongate handle, a paddle head, and an absorbent material that wraps around the paddle head. A score line is included between the paddle head and the elongate handle that allows the user to snap off the paddle head from the elongate handle. The disadvantage of this design is that while the sampling device with a thicker wall of plastic at the score line can withstand greater force when the user presses on the sampling device, the greater wall thickness at the score line makes it difficult to break away the head away from the handle after the sample is collected. On the other hand, a thinner wall at the score line makes the paddle head susceptible to breaking away the paddle head from the handle while the sample is being collected if the user presses hard on the surface to disrupt the biofilm. Consequently, the design is not desirable since it is imperative that the score line thickness be precisely accurate to avoid inadvertent breakage during sampling while maintaining sufficient durability to remain intact when the user presses and scrubs against the surface for sampling.

The other disadvantage of the sampling device with a snap-off head is that the absorbent material is affixed to the paddle head using an adhesive or sonic welding between the absorbent material to the plastic portion of the paddle head. Bonds between absorbent materials and the plastic used for the paddle head are typically weak. Therefore, the sponge may easily detach from the plastic paddle head during sampling or rubbing against rough surfaces.

Therefore, the ideal device for collecting and sampling should be durable and strong enough to withstand the pressure applied by the user pressing on the collection device without breaking or snapping off from the handle. The ideal collection device would be designed in a way that the device can be easily inserted into a hard-to-reach area with minimal concern that it will be caught or that portions of the device will be left behind after the sample is collected. The ideal collection device would be designed and constructed in a manner that resists breakage, yet affords sufficient flexibility to collect samples around a bend or corner in production equipment. Moreover, the collection device would be easy to use and present minimal opportunity for the collection device to get caught in equipment when collecting samples. The ideal collection device further would be effective in collecting from rough and/or wide surfaces such as concrete floors or evaporation coil fins in refrigeration units without the absorbent material abrading and tearing away from the handle. The ideal collection device would be capable of easily detaching from the handle without the need for the user to touch the sample, in order to prevent contamination. The ideal collection device would be modular to accommodate different sizes of paddle heads for providing flexibility in use.

The present invention incorporates a design in which the absorbent material used for collection is directly bonded to itself. The strongest bonds and the greatest flexibility in the choice of adhesives are obtained when the adhesive can be applied to two areas of the same material. Bonding of the absorbent material to itself strongly affixes the absorbent to the sampling device to withstand the pressure applied by the user during sampling. The present invention is directed to fulfilling all of these needs and others as described below.

SUMMARY OF THE INVENTION

In accordance with the present invention, a device for collecting samples is provided having a detachable handle with a threaded portion and a tip protruding adjacently from the threaded portion. The device for collecting samples is further provided having a connecting head with a receiving member whereby the receiving member detachably engages the threaded portion of the handle. The connecting head further comprises a hollow pocket through which the tip of the detachable handle fits before locking the detachable handle to the connecting head. The detachable handle further comprises a pair of wings extending laterally at a distal portion of the handle with a perpendicular edge that is substantially similar in width as the connecting head to prevent the connecting head from catching at hard-to-reach areas or detaching from the handle. The absorbent material is placed about the connecting head wherein the absorbent material is a single piece of generally rectangular material folded at a distal edge of the connecting head and adhered through a first and second aperture of the connecting head. The detachable handle further comprises a locking member adjacent to the threaded portion of the detachable handle for locking the detachable handle to the connecting head by internally clicking the locking member into a protruding member of the connecting head.

The detachable handle with the threaded portion is releasably attached to a connecting head with an absorbent material by rotating the detachable handle into the connecting head by 180 degrees in a clockwise direction. By holding the detachable handle, the connecting head with the absorbent material is rubbed against a surface with the absorbent material on the connecting head of the device for collecting samples. After collecting the sample, the connecting head and absorbent material containing the sample is placed into a sterile, collection bag. A user can hold the connecting head with the absorbent material from the outside of the collection bag without directly touching the absorbent material. The user can grasp the detachable handle, rotate the handle in a counter-clockwise direction while holding the connecting head still, detach the handle from the connecting head, and leave the connecting head with the absorbent material in the collection bag.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

The accompanying drawings, which are incorporated in and constitute a part of this specification, illustrate various exemplary embodiments.

Similar reference characters denote corresponding features consistently throughout the attached drawings.

DETAILED DESCRIPTION OF THE INVENTION

The detailed description set forth below in connection with the appended drawings is intended as a description of presently preferred embodiments of the invention and is not intended to represent the only forms in which the present invention may be constructed and/or utilized. The description sets forth the functions of and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The present invention is directed to sampling devices, and more particularly to a device for collecting samples that is ideally suited for use in sterile collection in preventing and monitoring contamination of certain areas. The device for collecting samples 50 may be used for collecting any samples including microorganisms and other types of samples on larger surfaces.

Figures 1A, 1B:
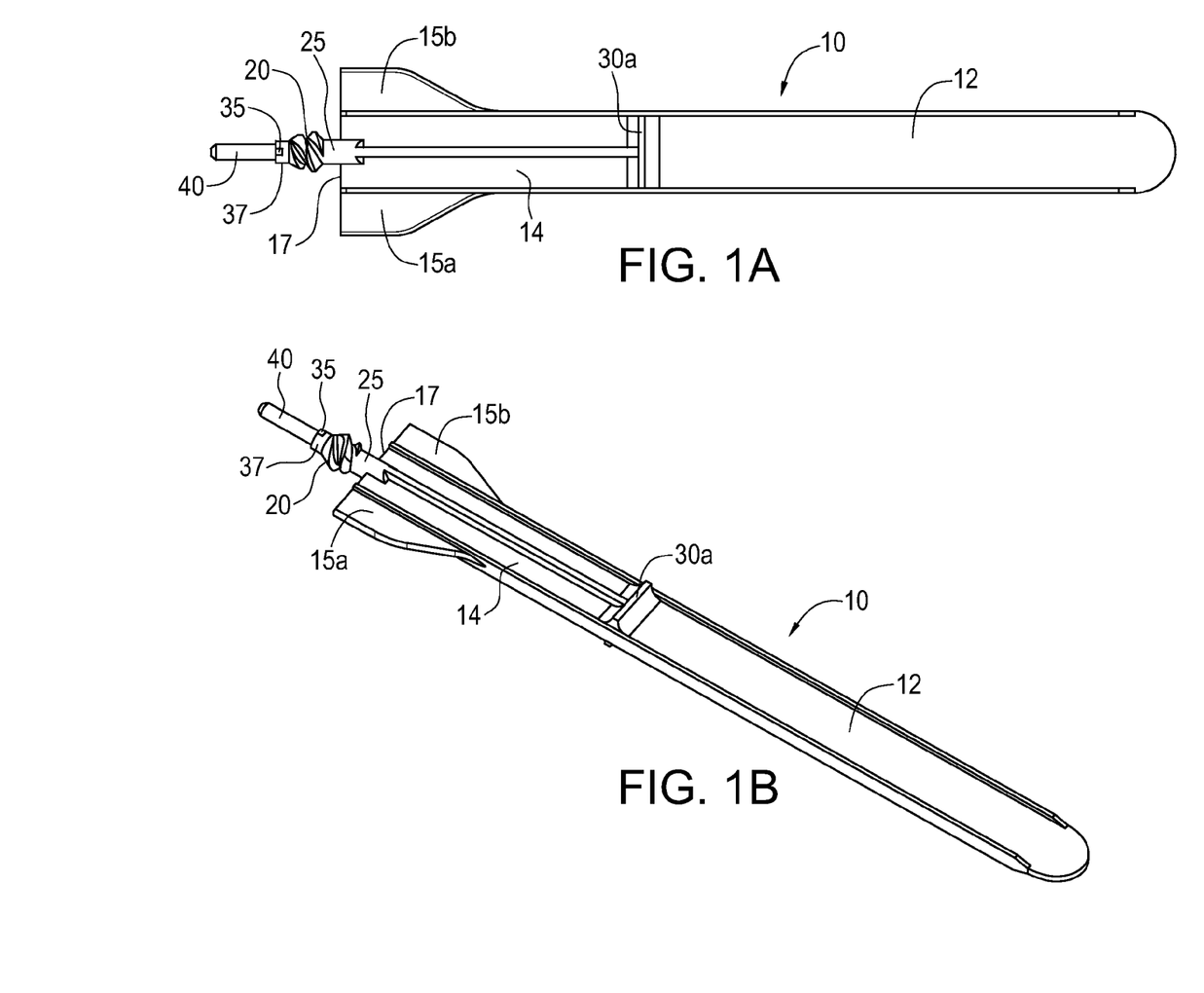
FIG. 1A is a top view of one embodiment of a handle in accordance with the present invention.
FIG. 1B is a perspective view of one embodiment of a handle in accordance with the present invention.

Referring to FIG. 1A, a top view of the detachable handle 10 of the device for collecting samples 50 is shown. The detachable handle 10 is comprised of a proximal portion 12, a distal portion 14, a notch 30 located between the proximal portion 12 and the distal portion 14, a pair of wings 15a, 15b located on the distal end of the distal portion 14 with a perpendicular edge 17, and a tip 40 with a threaded portion 20 connected to the distal portion 14 extending from the perpendicular edge 17. The detachable handle 10 is generally flat with rounded corners on the proximal portion 12 and has a straight, perpendicular edge at the distal portion 14 with gradual widening of the wings 15a, 15b at the lateral sides of the distal portion 14.

Figure 1C:
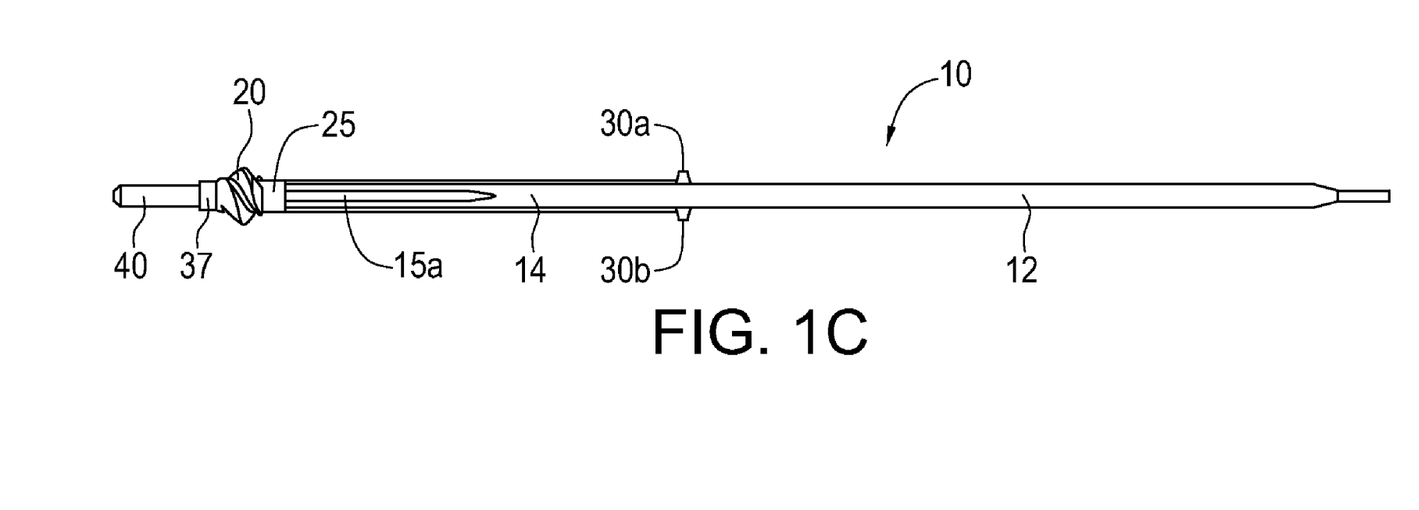
FIG. 1C is a side view of one embodiment of a handle in accordance with the present invention.
Figure 1D:
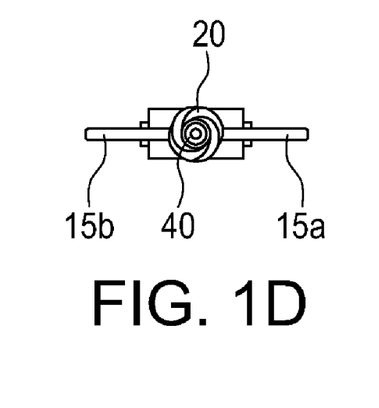
FIG. 1D is a front view of one embodiment of a handle in accordance with the present invention.

In one embodiment, the detachable handle 10 is formed of a rigid material such as polystyrene, polycarbonate, polyethylene, polypropylene, or ABS (Acrylonitrile-Butadiene-Styrene). The notch 30 is located approximately midway between the proximal portion 12 and the distal portion of the handle 10 to provide a reference point for a user to insert the device 14 in hard-to-reach areas and also to hold the handle 10 while collecting samples. As shown in FIGS. 1B-1C, the notch 30a, 30b on an upper side and lower side of the detachable handle 10 is slightly elevated from the flat handle 10 for an easy grip of the detachable handle 10 and for point of reference during use.

Continuing down to the distal portion 14 of the detachable handle 10, the first and second wings 15a, 15b on each side of the distal portion 14 span the width of the connecting head 100 (shown in later FIGS.) to prevent the connecting head 100 from detaching from the handle 10 or catching on protruding areas of the manufacturing equipment while sampling from difficult-to-access areas. More specifically, the perpendicular edge 17 of the distal portion 14 of the handle 10 is substantially similar in width to the distal edge 145 and proximal edge 155 of the connecting head 100 to prevent the connecting head 100 from catching at difficult-to-reach areas and/or detaching from the detachable handle 10. The tip 40 with the threaded portion 20 is integrally connected to the distal portion 14 extending from the perpendicular edge 17 that fits with the connecting head 100.

The tip 40 is substantially cylindrical in shape with a locking member 35 on an intermediate portion 37 centrally located adjacently inbetween the tip 40 and the threaded portion 20. The intermediate portion 37 is slightly thicker in diameter than the tip 40 with a locking member 35 on one side or both top and bottom sides of the intermediate portion 37. The threaded portion 20 is slightly thicker in diameter than the intermediate portion 37 to engage the matching threaded surface 125 (as shown in later FIGS.) of the receiving member 120 of the connecting head 100. The threaded portion 20 continues as a smooth portion 25 that is integrally connected to the perpendicular edge 17 of the distal portion 14 of the detachable handle 10. The diameter of the intermediate portion 37 and the smooth portion 25 are substantially similar.

Referring to FIGS. 1A to 1D, in one embodiment of the present invention, the detachable handle 10 is approximately 6.3 inches long, 0.15 inches thick, and 0.625 inches wide. The length of the tip 40 is approximately 0.55 inches and the diameter of the tip 40 is approximately 0.12 inches. The length of the tip 40, threaded portion 20, and intermediate portion 37 is approximately 0.98 inches. The dimensions of this handle 10 are not meant to be limiting and the size of the detachable handle 10 may be changed accordingly to accommodate different areas and to use with varying shapes and sizes of the connecting head 100.

Figure 2A:
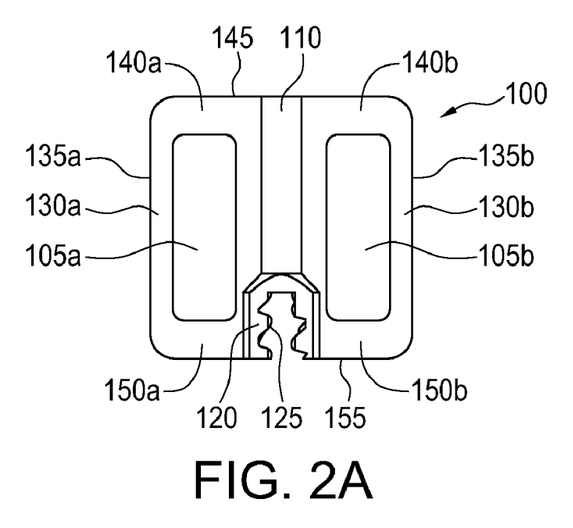
FIG. 2A is a top view of one embodiment of a connecting head in accordance with the present invention.
Figure 2B:
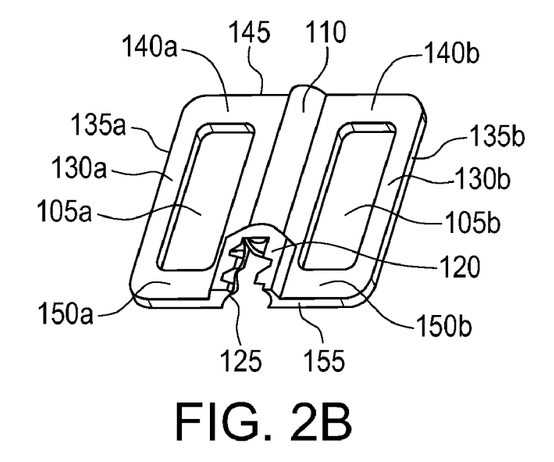
FIG. 2B is a perspective view of one embodiment of a connecting head in accordance with the present invention.
Figure 2C:
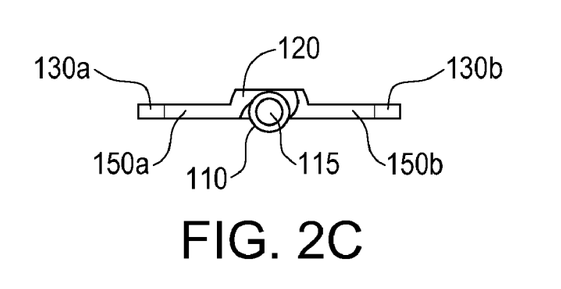
FIG. 2C is a back view of one embodiment of a connecting head in accordance with the present invention.

Referring to FIGS. 2A to 2C, the connecting head 100 is generally rectangular and flat in shape with rounded edges comprising a cylindrically hollow pocket 110 to receive the tip 40, first and second apertures 105a, 105b, and a receiving member 120 with a matching threaded surface 125 to receive the threaded portion 20. Around the apertures 105a, 105b, the connecting head 100 includes distal sides 140a, 140b, outer sides 130a, 130b, and proximal sides 150a, 150b spanning the width of the perpendicular edge 17 of the detachable handle 10.

Figure 5A:
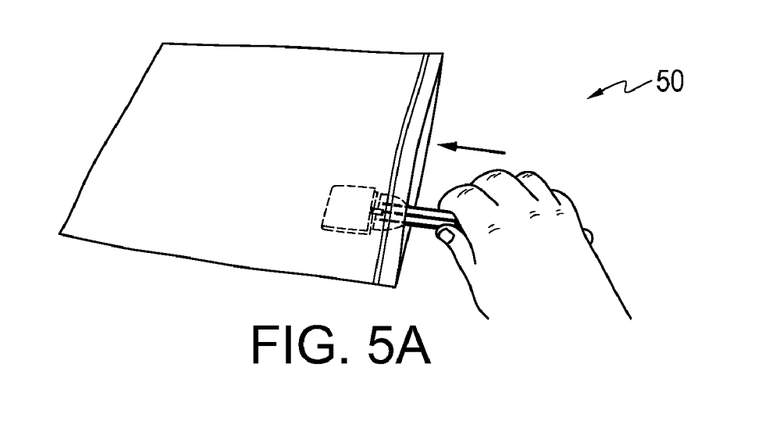
FIGS. 5A-5C are perspective views of a method of using the device in accordance with FIGS. 1-4.
Figure 5B:
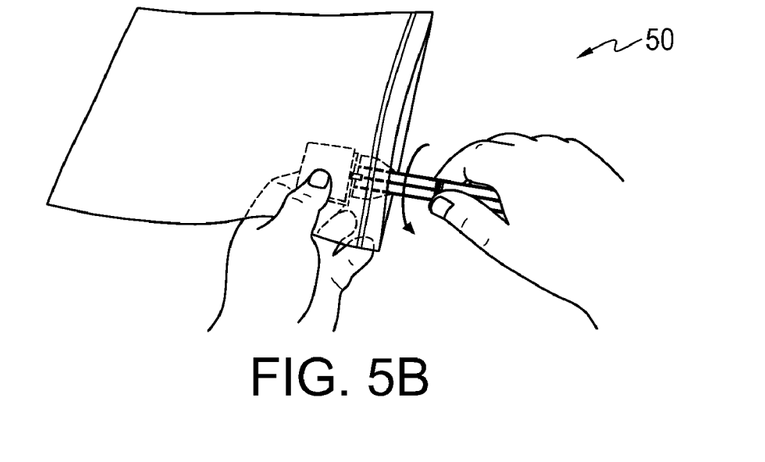
Figure 5C:
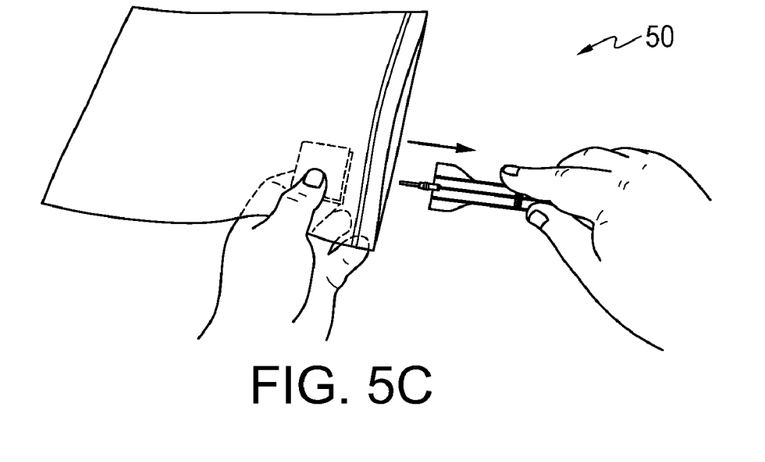

The connecting head 100 has a hollow cylindrical pocket 110 that is centrally and axially located along the middle portion of the connecting head 100 to receive the tip 40. The distal end of the receiving member 120 of the head 100 also receives the intermediate portion 37 with a locking member 35 and the immediately adjacent threaded portion 20. The user may insert the tip 40 into the channel 115 of the cylindrically hollow pocket 110 and rotate the handle 10 by 180 degrees in a clockwise direction to removably engage the threaded portion 20 against the matching threaded surface 125 of the receiving member 120. When the handle 10 is rotated in the receiving member 120 by 180 degrees in a clockwise direction, the locking member 35 with an indentation located on the intermediate portion 37 of the handle 10 also securely engages and clicks into place with an internally protruding member (not shown in these FIGS.) to removably hold the connecting head 100 with the handle 10. Similarly, the handle 10 may be held and rotated by 180 degrees in a counter-clockwise direction to release the connecting head 100 from the handle 10 after collecting samples. The release action of the connecting head 100 after collecting the sample will be more readily understood as shown in FIGS. 5A-5C. The degrees of rotation between the handle 10 and the receiving member 120 are not meant to be limiting and the degrees of rotation for engaging the handle 10 to the connecting head 100 may be changed accordingly to accommodate different degrees for engagement. In one embodiment, the connecting head 100 is approximately 0.26 inches long, 1.26 inches wide, and 0.065 inches thick. The diameter of the channel 115 is similar to that of the tip 40 so that the channel 115 can accommodate the tip 40. The first and second apertures 105a, 105b are approximately 0.9 inches long and 0.3 inches wide. The outer sides 130a, 130b are approximately 0.11 inches wide. The first and second wings 15a, 15b span the same width of the connecting head 100, and the perpendicular edge 17 is approximately 1.26 inches long to substantially match the width of the connecting head 100 from the first outer edge 135a to the second edge 135b of the connecting head 100. The dimensions of the connecting head 100 are not meant to be limiting and the size of the connecting head 100 may be easily adjusted to accommodate different areas and to use with varying sizes and shapes of the detachable handle 10.

Figure 3:
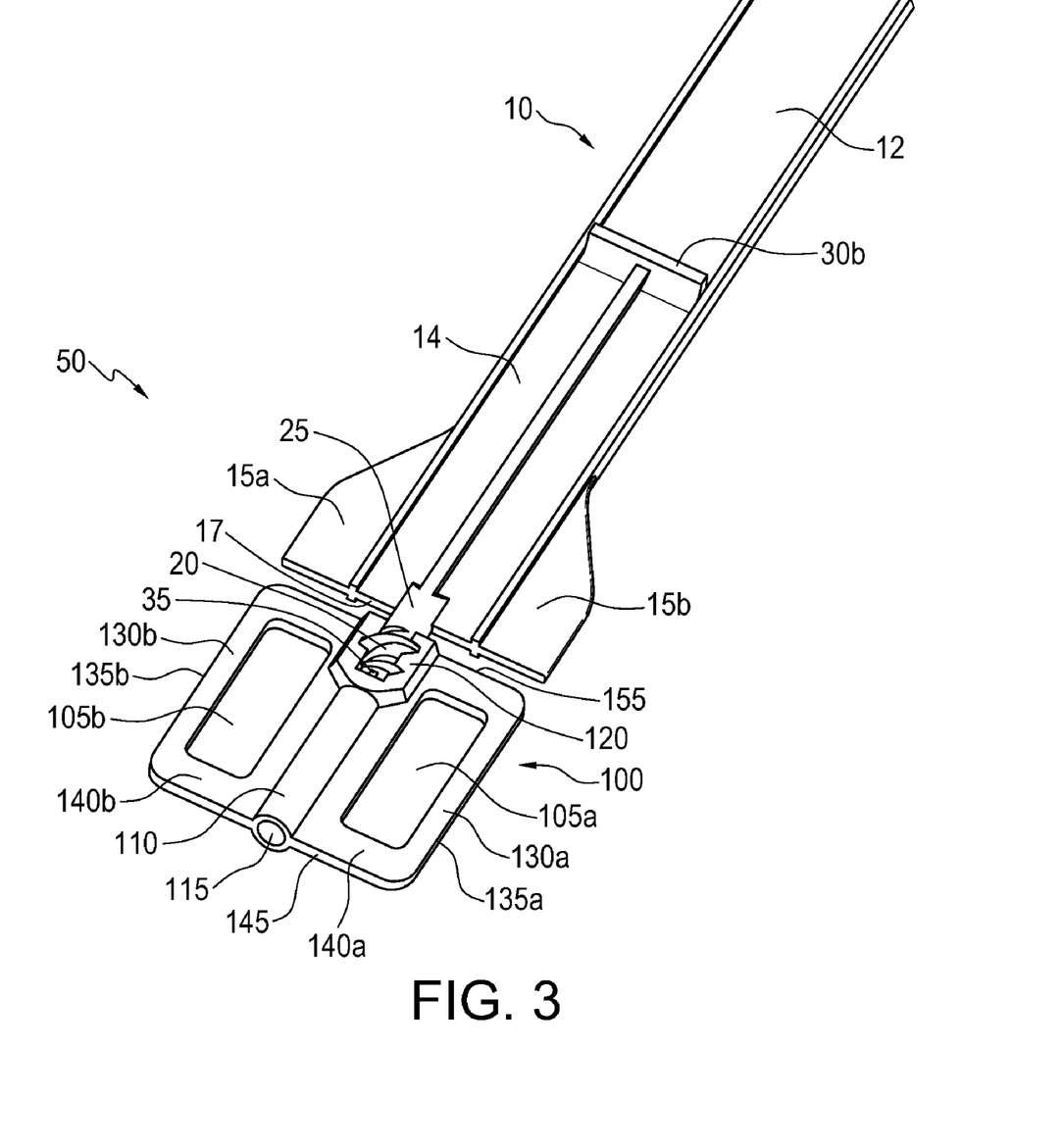
FIG. 3 is a perspective view of one embodiment of a device for collecting samples without an absorbent material in accordance with the present invention.

In the embodiment of FIG. 3, the assembled device for collecting samples 50 is shown without the absorbent material 200. The detachable handle 10 is assembled and removably attached to the connecting head 100 after the detachable handle 10 is rotated by 180 degrees in a clockwise direction in connection with the connecting head 100. The channel 115 of the hollow pocket 110 retains the tip 40 of the detachable handle 10, and the threadable portion 20 engages the receiving member 120. The tip 40 is first inserted into the channel 115 and the handle 10 is rotated in a clockwise direction to engage the threadable portion 20 with the matching threadable surface 125 of the receiving member 120. The detachable handle 10 is securely and removably locked or clicked into the connecting head 100 by the locking member 35 gently clicking into place with an internal protruding member (not shown in FIGS.) of the receiving member 120 of the connecting head 100. Gentle pressure applied in a counter-clockwise direction and rotating of the handle 10 in a counter-clockwise direction are required to release the connecting head 100 from the handle 10 when the connecting head 100 is ready to be released after collecting a sample on the absorbent material 200.

Figure 4:
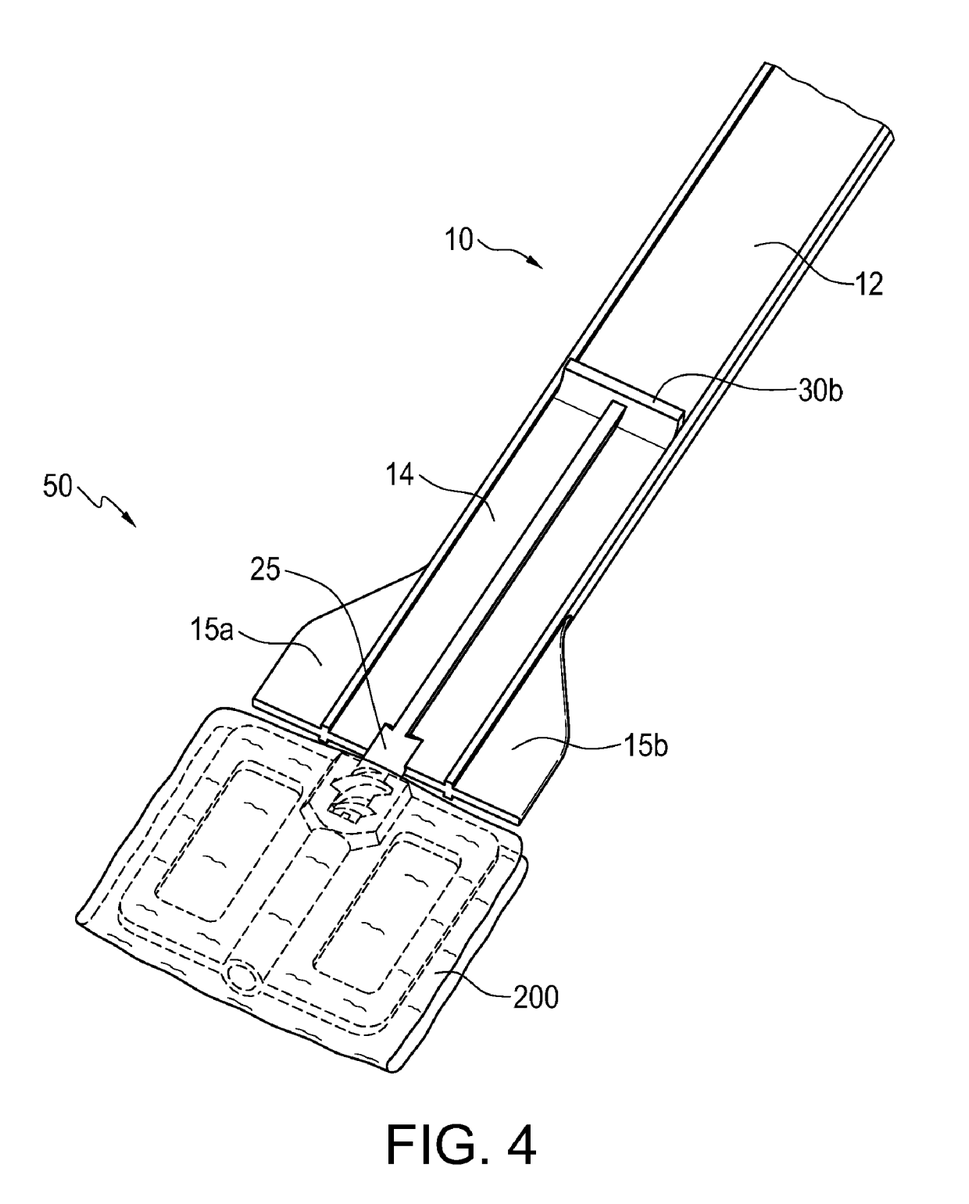
FIG. 4 is a perspective view of one embodiment of a device for collecting samples with an absorbent material in accordance with the present invention.

In the embodiment of FIG. 4, the assembled device for collecting samples 50 is shown with the absorbent material 200. The absorbent material 200 is a single piece of generally rectangular absorbent material folded and placed about the connecting head 100 at the distal edge 145. The absorbent material 200 is formed of an absorbent material, such as cellulose, polyurethane, polyester, gauze, or other similar material. The absorbent material 200 sufficiently covers the connecting head 100. More specifically, the absorbent material 200 folds over the distal edge 145 and comes up to the proximal edge 155 to sufficiently cover the connecting head 100. The space between the proximal edge 155 of the connecting head 100 and the perpendicular edge 17 of the distal portion 14 of the handle 10 is not covered by the absorbent material 200.

The absorbent material 200 adheres to the connecting head 100 by using a non-toxic adhesive on the inner side of the absorbent material 200 through the first and second apertures 105a, 105b. A short strip of adhesive may be applied on the first inner side of the absorbent material 200 through the apertures 105a, 105b so that when the absorbent material 200 is folded over at the distal edge 145, and the second inner side of the absorbent material 200 can easily adhere to the first inner side with the strips of adhesive through the apertures 105a, 105b. Therefore, the absorbent material 200 bonds directly to itself through the apertures 105a, 105b with adhesive inbetween and does not rely upon adhesion to the connecting head 100. If desired, adhesive can also be placed on the connecting head 100 to provide additional bonding between the absorbent material 200 and the connecting head 100.

With the current design of the present invention, there is usually no need to attach the absorbent material 200 to the connecting head 100. Typically, the bond between two different materials, the absorbent material 200 and the connecting head 100, is weaker than a bond between two layers of absorbent material. Additionally, an absorbent material-to-connecting head bond typically requires special manufacturing processes such as sonic welding, whereby the plastic of the connecting head 100 is melted using ultrasonic energy so that the melted plastic migrates a small distance into the absorbent material 200. Use of this two-material bond alone (i.e., without bonding the absorbent material to itself) is not recommended because the two-material bond is generally weaker and makes the absorbent material susceptible to tearing away or fragmenting during use in collecting a sample. In addition, sonic welding or other cumbersome two-material bonding processes are generally less convenient and more expensive than the process of bonding the absorbent material 200 to itself. Therefore, the single-piece of generally rectangular material of the absorbent material 200 is folded at a distal edge 145 of the connecting head 100 and is directly bonded to itself through the apertures 105*a*, 105*b* using a non-toxic adhesive prior to attaching the connecting head 200 to the detachable handle 10. Alternatively, two, separate pieces of the absorbent material 200 are directly bonded to itself through the apertures 105*a*, 105*b* using a non-toxic adhesive prior to attaching the connecting head 200 to the detachable handle 10.

Referring to FIG. 5A, a user collects a sample onto the absorbent material 200 and inserts the connecting head 100 of the device 50 into a sterile, sample collection bag. Prior to collecting a sample, the method of collecting samples using the present invention comprises the step of attaching the detachable handle 10 with the threadable portion 20 to the connecting head 100 to have the fully assembled device 50. The assembled device 50 with the connecting head 200 attached to the detachable handle 10 is then placed into a collection bag. Optionally, the absorbent material 200 placed about the connecting head 100 is hydrated with a culture broth for sampling dry surfaces. For all other surfaces of sampling, hydrating the absorbent material 200 is not necessarily required. The collection bag is then sealed and sterilized with the assembled device 50 in the collection bag prior to use. After sterilization of the assembled device 50 in the sealed collection bag, a user takes the assembled device 50 out of the collection bag and holds the detachable handle 10 to rub against a surface with the absorbent material 200 touching the surface for collecting samples.

After rubbing against the surface, the connecting head 100 and absorbent material 200 portion of the device is placed into a collection bag. Any flexible, sterile plastic bag may be used so that the device for collecting samples 50 can be inserted to prevent direct contact with the collected sample on the absorbent material 200 of the connecting head 100 for avoiding any contamination of the sample. After the connecting head 100 with the absorbent material 200 containing the sample is inserted into the sterile, sample collection bag, the user holds the connecting head 100 with one hand from the outside of the collection bag while the other hand is used to directly grasp the detachable handle 10. The user may rotate or twist the detachable handle 10 from the connecting head 100 by 180 degrees in a counter-clockwise direction. Rotating of the handle 10 in a counter-clockwise direction releases the detachable handle 10 from the connecting head 100 and leaves the connecting head 100 and absorbent material 200 containing the sample in the collection bag. Therefore, the user collects samples and deposits the sample in a sterile, collection bag without touching the absorbent material 200 containing the sample, preventing contamination during transportation for later examination and analysis.

The terms and expressions that have been employed in the foregoing specification are used as terms of description and not of limitation, and are not intended to exclude equivalents of the features shown and described or portions of them. The scope of the invention is defined and limited only by the claims that follow.

What is claimed is:

1. A device for collecting samples comprising:
   (a) a detachable handle with a threaded portion;
   (b) a connecting head with a receiving member, the receiving member detachably engaging the threaded portion of the handle;
   (c) an absorbent material placed about the connecting head; and
   (d) a locking member adjacent to the threaded portion of the detachable handle for locking the detachable handle to the connecting head;
   wherein the connecting head with the absorbent material is released from the detachable handle after collecting a sample.

2. The device for collecting samples according to claim 1, wherein the detachable handle further comprises a tip extending adjacently from the threaded portion.

3. The device for collecting samples according to claim 1, wherein the detachable handle further comprises a pair of wings extending laterally at a distal portion of the handle with a perpendicular edge that is substantially similar in width to the width of the connecting head to prevent the connecting head from catching in hard-to-reach areas.

4. The device for collecting samples according to claim 1, wherein the receiving member of the connecting head detachably engages the threaded portion of the detachable handle by rotating the detachable handle into the connecting head in a clockwise direction before locking the detachable handle to the connecting head.

5. The device for collecting samples according to claim 1, wherein the connecting head further comprises a hollow pocket through which the tip of the detachable handle fits before releasably locking the detachable handle to the connecting head.

6. The device for collecting samples according to claim 1, wherein the connecting head further comprises at least one aperture located inside of the connecting head.

7. The device for collecting samples according to claim 6, wherein the absorbent material is a single piece of generally rectangular material folded at a distal edge of the connecting head and directly adhered at inner sides of the absorbent material through the at least one aperture of the connecting head.

8. The device for collecting samples according to claim 6, wherein the absorbent material comprises two pieces of generally rectangular materials placed about the connecting head and directly adhered at inner sides of the absorbent material through the at least one aperture of the connecting head.

9. The device for collecting samples according to claim 1, wherein the absorbent material is formed of at least one of polyurethane, cellulose, polyester, and gauze.

10. The device for collecting samples according to claim 1, wherein the locking member of the detachable handle comprises a protrusion shaped to fit within the receiving member of the connecting head.

11. The device for collecting samples according to claim 1, wherein the connecting head is released from the detachable handle by rotating the detachable handle from the connecting head in a counter-clockwise direction.

12. A device for collecting samples comprising:
   (a) a detachable handle with a threaded portion and a tip protruding adjacently from the threaded portion;
   (b) a connecting head having at least one aperture and a receiving member, the receiving member detachably engaging the threaded portion of the handle by rotating the handle by 180 degrees in a clockwise direction before locking the detachable handle to the connecting head;
   (c) an absorbent material placed about the connecting head, the absorbent material being a single piece of generally rectangular material folded at a distal edge of the connecting head and adhered directly at inner sides of the absorbent material through the at least one aperture of the connecting head; and
   (d) a locking member comprises a protrusion located on an intermediate portion and adjacent to the threaded portion of the detachable handle for locking the detachable handle to the connecting head by internally clicking the locking member into an internally protruding member located within the receiving member of the connecting head;
   wherein the connecting head with the absorbent material is released from the detachable handle after collecting a sample by rotating the detachable handle from the connecting head by 180 degrees in a counter-clockwise direction.

13. The device for collecting samples according to claim 12, wherein the detachable handle further comprises a pair of wings extending laterally at a distal portion of the handle with a perpendicular edge that is substantially similar in width to the width of the connecting head, to prevent the connecting head from detaching from the handle and catching at difficult to reach areas.

14. A method of collecting samples using a device for collecting samples, comprising the steps of:
   (a) attaching a detachable handle with a threaded portion to a connecting head with an absorbent material placed about the connecting head and a receiving member that detachably engages the threaded portion to assemble the device for collecting samples;
   (b) rubbing against a surface with the absorbent material touching the surface for collecting samples;
   (c) placing the connecting head and absorbent material into a collection bag;
   (d) holding the connecting head from outside of the collection bag;
   (e) grasping the detachable handle to rotate the detachable handle from the connecting head in a counter-clockwise direction; and
   (f) releasing the connecting head with the absorbent material into the collection bag.

15. The method according to claim 14, wherein the step of attaching the detachable handle with the threaded portion to the connecting head with the absorbent material further comprises rotating the handle into the connecting head by 180 degrees in a clockwise direction.

16. The method according to claim 15, wherein the step of rotating the handle into the connecting head further comprises locking the detachable handle to the connecting head by internally clicking a locking member of the detachable handle comprising a protrusion shaped to fit within the receiving member of the connecting head.

17. The method according to claim 14, further comprising the step of sterilizing the assembled device prior to the step of rubbing against a surface with the absorbent material touching the surface for collecting samples.

18. The method according to claim 14, further comprising the optional step of hydrating the absorbent material placed about the connecting head with a culture broth for sampling dry surfaces prior to the step of rubbing against a dry surface.

19. The method according to claim 14, wherein the detachable handle further comprises a tip protruding adjacently from the threadable portion.

20. The method according to claim 19, wherein the connecting head further comprises a hollow pocket through which the tip of the detachable handle fits before locking the detachable handle to the connecting head.

21. The method according to claim 14, wherein the detachable handle further comprises a pair of wings extending laterally at a distal portion of the handle with a perpendicular edge that is substantially similar in width to the width of the connecting head to prevent the connecting head from catching in hard-to-reach areas.

22. The method according to claim 14, wherein the connecting head comprises at least one aperture.

23. The method according to claim 14, wherein the absorbent material is a single piece of generally rectangular material folded at a distal edge of the connecting head and adhered directly to itself through the at least one aperture of the connecting head.

24. The method according to claim 14, wherein the absorbent material comprises two pieces of generally rectangular materials placed about the connecting head and directly adhered at inner sides of the absorbent material through the at least one aperture of the connecting head.

* * * * *